(12) United States Patent
Kan

(10) Patent No.: US 6,932,772 B2
(45) Date of Patent: Aug. 23, 2005

(54) NONINVASIVE BLOOD PRESSURE MEASURING METHOD AND APPARATUS

(76) Inventor: Jie Kan, Ningxia Medical College, Yinchuan, Ningxia (CN), 750004

(*) Notice: Subject to any disclaimer, the term of this patent is extended or adjusted under 35 U.S.C. 154(b) by 0 days.

(21) Appl. No.: 09/978,345

(22) Filed: Oct. 16, 2001

(65) Prior Publication Data

US 2002/0026121 A1 Feb. 28, 2002

Related U.S. Application Data

(63) Continuation-in-part of application No. PCT/CN00/00097, filed on Apr. 21, 2000.

(30) Foreign Application Priority Data

Apr. 21, 1999 (CN) ........................................ 99105671 A
Apr. 21, 1999 (CN) ........................................ 99208086 U (51) Int. Cl.[7] ................................................. A61B 5/02
(52) U.S. Cl. ........................ 600/490; 600/485; 600/491; 600/499
(58) Field of Search ................................ 600/485–507; 602/5–12, 20–22

(56) References Cited

U.S. PATENT DOCUMENTS

| 4,369,774 A | | 1/1983 | Robbins | |
|---|---|---|---|---|
| 4,799,491 A | | 1/1989 | Eckerle | |
| 4,799,791 A | * | 1/1989 | Echizen et al. | 356/121 |
| 4,850,369 A | * | 7/1989 | Yamasawa | 600/499 |
| 4,869,261 A | * | 9/1989 | Penaz | 600/480 |
| 4,987,900 A | | 1/1991 | Eckerle et al. | |
| 4,993,422 A | * | 2/1991 | Hon et al. | 600/485 |
| 5,033,471 A | | 7/1991 | Yokoe et al. | |
| 5,054,495 A | * | 10/1991 | Uemura et al. | 600/493 |
| 5,170,796 A | * | 12/1992 | Kobayashi | 600/500 |
| 5,243,990 A | * | 9/1993 | Aung et al. | 600/490 |
| 5,497,779 A | | 3/1996 | Takaya et al. | |
| 5,772,601 A | | 6/1998 | Oka et al. | |
| 5,840,037 A | * | 11/1998 | Tochikubo et al. | 600/499 |
| 5,913,826 A | * | 6/1999 | Blank | 600/500 |
| 6,132,383 A | * | 10/2000 | Chesney et al. | 600/502 |
| 6,231,517 B1 | * | 5/2001 | Forstner | 600/485 |

FOREIGN PATENT DOCUMENTS

| CN | 2371945 Y | | 4/2000 | |
|---|---|---|---|---|
| JP | 05261074 A | * | 10/1993 | ......... A61B/5/0245 |
| WO | 97/12542 | | 4/1997 | |
| WO | WO 97/12542 | * | 4/1997 | ............ A61B/5/00 |

* cited by examiner

Primary Examiner—Robert L. Nasser
Assistant Examiner—Patricia Mallari
(74) Attorney, Agent, or Firm—Akerman Senterfitt (57) ABSTRACT

A method and a device for non-invasive blood pressure measurement wherein the angle between the hand and the wrist, and the turning angle of the wrist relative to the middle part of the forearm, are kept to the most suitable degree for measuring the blood pressure of the radial artery. At least one pressure bladder and one arterial pulse transducer array are placed on the skin over the radial artery of the wrist to apply the external pressure to the artery and to detect the change of the arterial pulse signals. This method and device can correctly measure the intermittent or continuous blood pressure of the radial artery or the ulnar artery based on the principles of oscillation method and volume compensation method, and effectively eliminate the influence on the measurement due to body movement and the influence on blood circulation and neural function of the hand caused by long-term blood pressure measurement.

32 Claims, 10 Drawing Sheets

NONINVASIVE BLOOD PRESSURE MEASURING METHOD AND APPARATUS

RELATED APPLICATIONS

This application is a continuation-in-part of international application number PCT/CN00/00097, filed Apr. 21, 2000.

FIELD OF THE INVENTION

This invention relates to a method and apparatus for non-invasive measurement of blood pressure, and, in particular, relates to a so-called oscillometric method and the corresponding apparatus for intermittent measurement of arterial blood pressure, as well as a so-called vascular unloading method and the corresponding apparatus for continuous measurement of arterial blood pressure.

BACKGROUND OF THE INVENTION

The oscillometric method is based on the principle that the blood vessel will be the most flexible (This state is called the "unloading state") and will be flattened separately when the external pressure of the artery is equal to the mean blood pressure and higher than the internal systolic blood pressure. Since the internal blood pressure of the artery is changing periodically along with the heart beat at all time (during a heartbeat cycle, the highest pressure is called systolic blood pressure, the lowest pressure is called diastolic blood pressure, and the average of the all pressure value over the heartbeat cycle is called the mean blood pressure), and the diameter (or volume) is changing periodically with the blood pressure so as to form the arterial pulse. The amplitude of the pulse will be maximum when the external pressure of the vessel is equal to the mean blood pressure so that the vascular wall is the most flexible, and the amplitude of the pulse will disappear when the external pressure of the vessel is higher than the systolic blood pressure so that the blood vessel is flattened. When measuring the blood pressure by using oscillometric method, at first, an air bladder (or liquid bladder) to apply the external pressure to the artery is fixed on the skin over the artery. Then the pressure of the bladder is changed. At the same time, the change in pulse amplitude is measured by a pulse transducer during the entire course. If the bladder pressure can be transmitted accurately to the outside of the blood vessel through the soft tissues under the center of the bladder and the pulse transducer can detect the arterial pulse from these soft tissues, the pressure will be equal to the mean blood pressure and the systolic blood pressure separately when the pulse amplitudes are at their maximum and close to disappearance. Therefore, the mean blood pressure and the systolic blood pressure can be measured by measuring the bladder pressure at the two moments using a pressure transducer. Furthermore, the diastolic blood pressure can be obtained by using some estimation algorithm. This method can only measure blood pressure intermittently because each process of pressure change for one cycle of measurement of the blood pressure needs a considerable amount of time.

Vascular unloading method is based on the principle that the diameter of the blood vessel will not change with the wave of the blood pressure in the vessel (or will not pulsate), but will maintain at its unloading state when the pressure outside the vessel is equal to the internal blood pressure at any given time. This method includes an air bladder (or liquid bladder) that applies the external pressure to the artery and a pulse transducer, and a feedback control system which uses the measured artery pulse to control the pressure of the air bladder. When measuring the blood pressure continuously by using vascular unloading method, at first, like the oscillometric method, the air bladder pressure is changed in a certain range, and at the same time, the change in pulse amplitude in the bladder pressure is measured. When the bladder pressure is equal to the mean pressure in the artery so that the vascular wall is the most flexible, and the amplitude of the pulse is the highest, the feedback control system is connected to magnify the measured signal of the pulse and phase compensate. The feedback control system is further used to control the bladder pressure so that it will change according to the pulse wave on the base of the mean pressure. Once the wave of the pressure on the outside of the blood vessel is made the same as the wave of the periodical change of the blood pressure inside the artery, both in shape and amplitude, so that the force on both the inside and outside the vessel wall reaches a dynamic balance, the diameter of the artery vessel, instead of changing with the wave of the intra-vascular blood pressure, will be maintained at its unloading state; i.e. the pulse oscillation amplitude is near zero. At this time, if the bladder pressure is continuously measured by a pressure transducer, the continuous measurement of the instantaneous blood pressure (i.e. blood pressure wave) can be obtained.

The two methods mentioned above are not currently used on the upper arm where the blood pressure is normally measured, but on the finger to measure the blood pressure of the finger artery. This is mainly because that the position of the brachial artery of the upper arm is very deep, so that the external pressure must be applied to the upper arm from all-rounded or near all-rounded of the arm, so as to transmit adequately the external pressure to the brachial artery. Because of the pressure, long-term frequent use of the oscillometric method to measure the blood pressure intermittently or keeping using the oscillometric method to measure the blood pressure continuously will all seriously affect the blood circulation and nerval function of the entire lower arm and the hand. However, the position of the finger artery is shallow, when measuring the finger blood pressure, the influence on the blood circulation and nerval function of the finger, caused by the increased bladder pressure, is smaller.

Numerous clinical experience results have shown that the two methods have another big problem when the finger is used for measuring blood pressure, that is, because the finger artery belongs to distal arteriolar, comparing with the so-called "system blood pressure" (or the blood pressure of the aorta near the heart) that is used clinically when judging whether the patient's blood pressure is normal or not, blood pressure of finger is around 10 mmHg lower under normal conditions. In case of arteriosclerosis, the difference can reach several ten mmHg. More importantly, because the composition of the smooth muscle inside the small artery vessel wall is larger than that in the aortal wall, and these vascular smooth muscle are very easily affected by various factors (such as coldness, anesthesia, etc.) so as to either produce vasoconstriction or vasodilation, which causes the blood pressure in the small artery to wave at a great range, under many circumstances, the blood pressure obtained from finger artery cannot be used to reflect the system blood pressure of the patient. Especially when the patient's circulation function is very weak, the finger artery can sometimes cause the loss of blood in the artery due to the extreme vasoconstriction of the vascular smooth muscle, so the blood pressure cannot be measured on the finger.

In order to correctly reflect the system blood pressure while not affecting the blood circulation of the distal part of the measured area, a proposal to change the measuring position of the two methods to the wrist has recently been made, and also changing the traditional all-rounded pressure bladder to a local pressure bladder so as to only give pressure to one of the two arteries in the wrist (radial artery and ulnar artery) has been considered. This is based on two points: first, the diameter of the radial artery or ulnar artery is much bigger than the finger artery, and the composition of the smooth muscle in the vessel wall is less than in the finger artery, so their blood pressure is closer to the system blood pressure than that of the finger artery, and also not easily affected by other factors. In addition, even when the patient's circulation function is very weak, the pulse can be always detected from the radial artery or ulnar artery, making the measurement of the blood pressure possible.

Secondly, normal people have more than two bigger arteries and veins on the wrist, of which, two arteries (radial artery and ulnar artery) are connected to each other by two arterial arches in the palm; several veins on the back of the hand are also connected to each other by the vain web on the back of the hand. The connection of the these blood vessels guarantees that, even if one artery and/or part of the vein is occluded (has an occlusion) for a long time, but the other artery and the rest parts of the veins will still have a smooth blood flow, the circulation of the hand will basically not be affected. Therefore, frequent and continuous blood pressure measurement can be performed for a long time with these two methods on one wrist artery of either the radial artery or ulnar artery.

Although related researches have shown that the mean blood pressure, systolic blood pressure, or the blood pressure wave can be separately and accurately measured, with oscillometric method and vascular unloading method, on the radial artery near the most protuberant spot on the volar aspect of the distal end of the radius, research has also discovered that it is actually very difficult to measure the blood pressure accurately on the wrist. It is mainly because the precision of the blood pressure measurement is very sensitive to the measuring position, so even on the most protuberant spot on the volar aspect of the distal end of the radius, on various positions with a difference of only 2,3 mm among them, the measured blood pressure can be greatly different. In addition, the precision of the measurement can also be affected by outside factors. First, the measured blood pressure will vary greatly when the wrist turns with the long axis of the forearm as the axis of rotation, or when the hand bends towards the palm side or the back side of the hand. Secondly, along with the increased bladder pressure, the bladder might move towards not only the center of volar aspect of wrist along the circumferential direction, but also the hand along the long axis of wrist. All these movements may change the bladder volume, and the movement in the direction of circumference and long axis may also cause the pulse transducer to move its position. Among these, the position change of the pulse transducer may affect the measuring precision of the oscillometric method and the vascular unloading method.

SUMMARY OF THE INVENTION

The goal of the invention is to provide a method and a device which can make use of the principles of the oscillometric method and the vascular unloading method to, simply and accurately, measure the intermittent or continuous blood pressure of the radial and/or the ulnar artery without obvious influence of the above mentioned factors, and also effectively eliminate the influence on the blood circulation and nerval function of the hand due to long-term, continuous measurement.

To reach the above-mentioned goal, the solution has been invented as follows:

1. At least, the angle between the wrist and the hand is kept to the most suitable degree for measuring the blood pressure of the radial artery. In addition, it is preferred to keep the turning angle of the wrist relative to the middle part of the forearm to the most suitable degree for measuring the radial arterial blood pressure. When measuring the blood pressure repeatedly or continuously for a long-term, in order to guarantee the above-mentioned location for the measurement on the wrist, this invention also uses a wrist holding bracket to hold the wrist bending position of the and the hand turning angle so that when the patient moves, the position of the pressure bladder and the pulse transducer, as well as the tendon, nerves, and radius in the wrist relative to the radial artery, stays the same during the measurement.

2. It is preferred to fix a pulse transducer array on the center of the pressure area of the pressure bladder placed on the skin over the radial artery of the wrist When changing the bladder pressure, the pulse signals of the radial artery are measured from many different positions on the wrist by the pulse transducer array through the entire bladder pressure changing process. These signals are feed to an optimal site selector to find easily the optimal site to most accurately measure the blood pressure of the radial artery.

3. In order to avoid the moving of the pressure bladder in the direction of the wrist's long axis towards the hand during the bladder inflation, the difference between the diameter of the wrist joint section and that of the middle part of the forearm is eliminated. Furthermore, the sinking surface of the dorsal side of the wrist joint section due to the hand bending is filled to a regular column surface.

4. In order to reduce the pain and numbness due to long-term continuous pressure still on one site, two pressure bladders are separately placed on both the radial and ulnar artery so that the blood pressure can be measured alternately on the two arteries. Because it is difficult to measure the blood pressure accurately on the ulna artery, the result of the blood pressure measured from the radial artery is used to calibrate the result measured from the ulnar artery.

DETAILED DESCRIPTION OF THE INVENTION

The First Embodiment

The first embodiment of this invention is a method and an apparatus for non-invasive, intermittent measurement of the blood pressure on the wrist with the oscillometric method.

Figure 1:
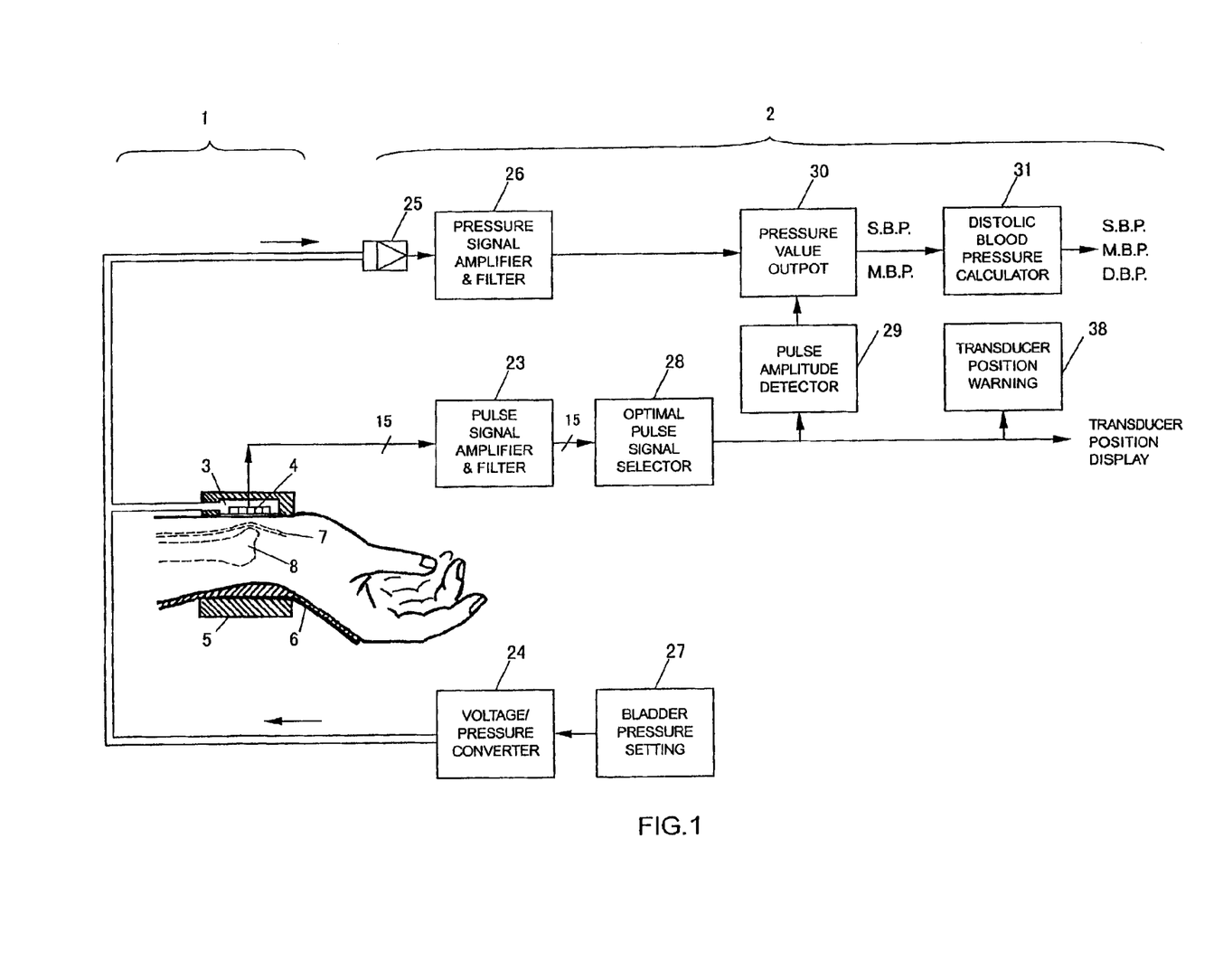
FIG. 1: the simplified block diagram of the first embodiment of this invention.
Figure 6:
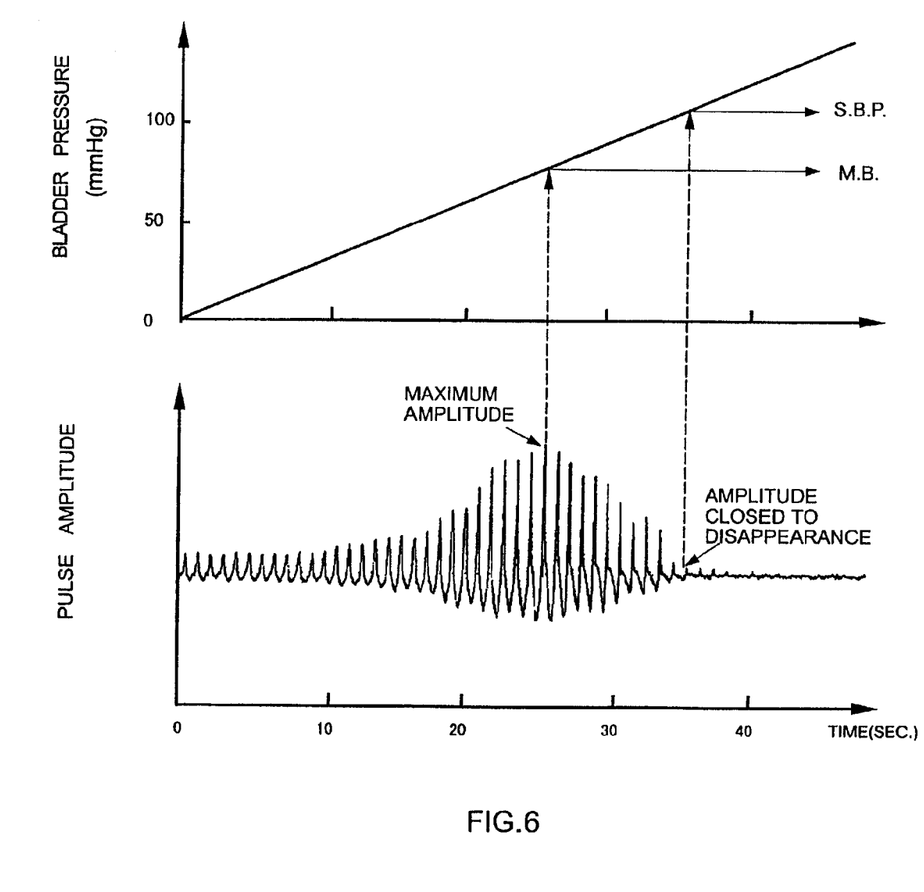
FIG. 6: the schematic illustration of the method for measuring the mean blood pressure and systolic blood pressure of the first embodiment shown in FIG. 1.

The non-invasive blood pressure measurement method of this embodiment, as shown in FIG. 1 and FIG. 6, comprise the following steps:

A. Keeping the angle between the wrist 18 and the hand 17 and the turning angle of the wrist 18 relative to the forearm 19 to the most suitable degree for measuring the blood pressure of the radial artery;

B. At least, placing a pressure bladder 3 and a pulse transducer array 4 on the skin over the crossing of radial artery and the most protuberant spot on the volar aspect of the distal end of the radius 7, and keeping the position of the transducer array and the bladder relative to the site to unchanged;

C. Changing the pressure in the pressure bladder 3 within the range that the lower limit is lower than the possible mean pressure of the subject, and the upper limit is higher than the subject's possible systolic blood pressure;

D. Along with the bladder pressure changing, detecting the pulse signals of the radial artery by the pulse transducer array 4 from many different positions on the wrist, and are feed to the optimal site selector 28 to find the optimal site for accurately measuring the blood pressure of the radial artery and the optimal pulse signal measured at the optimal site; and E. Applying the optimal pulse signal measured at the optimal site to the non-invasive measurement of the radial artery blood pressure. In this embodiment, the optimal pulse signal is applied to the non-invasive measurement of the mean blood pressure and the systolic blood pressure with the oscillometric method.

In the step A, at least, the angle between the wrist 18 and the hand 17 should be kept to form an angle between approximately 100 and 170 degrees. The angle can lower effectively the position of the tendon and the nerves by the radial artery, and cause the radial artery to be placed to a position nearest to the radius below it, so that the bladder can press the radial artery effectively.

Combine with the angle between the dorsal side of the wrist 18 and the dorsal side of the hand 17, to keep either the turning angle of the wrist 18 relative to the forearm 19 to be an angle between approximately 30 and 100 degrees towards the medial side of body, or the deflecting angle from the central line of the hand 17 in relative to the central line of the volar side of the wrist 18 to be an angle between approximately 10 and 40 degrees towards the little finger can further cause the radial artery to close up the radius.

In fact, it is most suitable for measuring the blood pressure of the radial artery if the above-mentioned three angles are used jointly to determine the posture of the wrist. To find the optimal site for accurately measuring the blood pressure of the radial artery, it is necessary that there are more than 2 columns and more than 2 lines site along the directions parallel and vertical to the radial artery respectively.

Because the amplitude of the pulse signal measured by the transducer near the radial artery is large, and the mean and systolic blood pressure corresponding the pulse signal measured on the site, where the pressure transmission is optimal, are lower, the method to select the optimal site and the optimal pulse signal measured at the optimal site comprise the following steps:

First, selecting a column of site from all columns of site, where detected the pulse signal possess the maximum oscillation during the change of the bladder pressure, and the amplitude during the maximum oscillation are the largest comparing with the amplitude of the pulse signal detected from other column of site;

Secondly, selecting a optimal site from the selected columns of site, where detected the pulse signal possess the amplitude being closed to disappearance during the bladder pressure is higher than the pressure corresponding to the maximum amplitude (shown in FIG. 6), and the bladder pressures corresponding to the maximum and the disappearance of the pulse signal detected at the site are the lowest comparing with the bladder pressures corresponding to the maximum and the disappearance of the pulse signal detected at other sites of the selected columns of the site;

Finally, the pulse signal detected at the optimal site is used for the optimal pulse signal.

After selecting the optimal site, the position of the optimal site in the pressure area of the pressure bladder is display in the most visual way. When setting bladder 3, the position of the bladder 3 is adjusted according to the display so that the optimal site is positioned in the center of the pressure bladder where the pressure transmission is most deep.

When this embodiment is applied to long-term measurement of the blood pressure, automatic check should be done to make sure that the optimal site is at the center of the pressure bladder 3. If optimal site shifts away from the center of the pressure bladder, a warning signal should be given so as to remind the operator to readjust the position of the pressure bladder 3.

As shown in FIG. 1, the apparatus based on the method above-mentioned in this embodiment comprising two parts: Part I is a wrist detecting assembly 1 for applying the external pressure and detecting the arterial pulse; Part II is a pressure feeding-measuring system 2 to feed the pressure to bladder 3 and measure both the bladder pressure and the radial arterial pulse signals for the blood pressure measurement of the radial artery.

Figure 2:
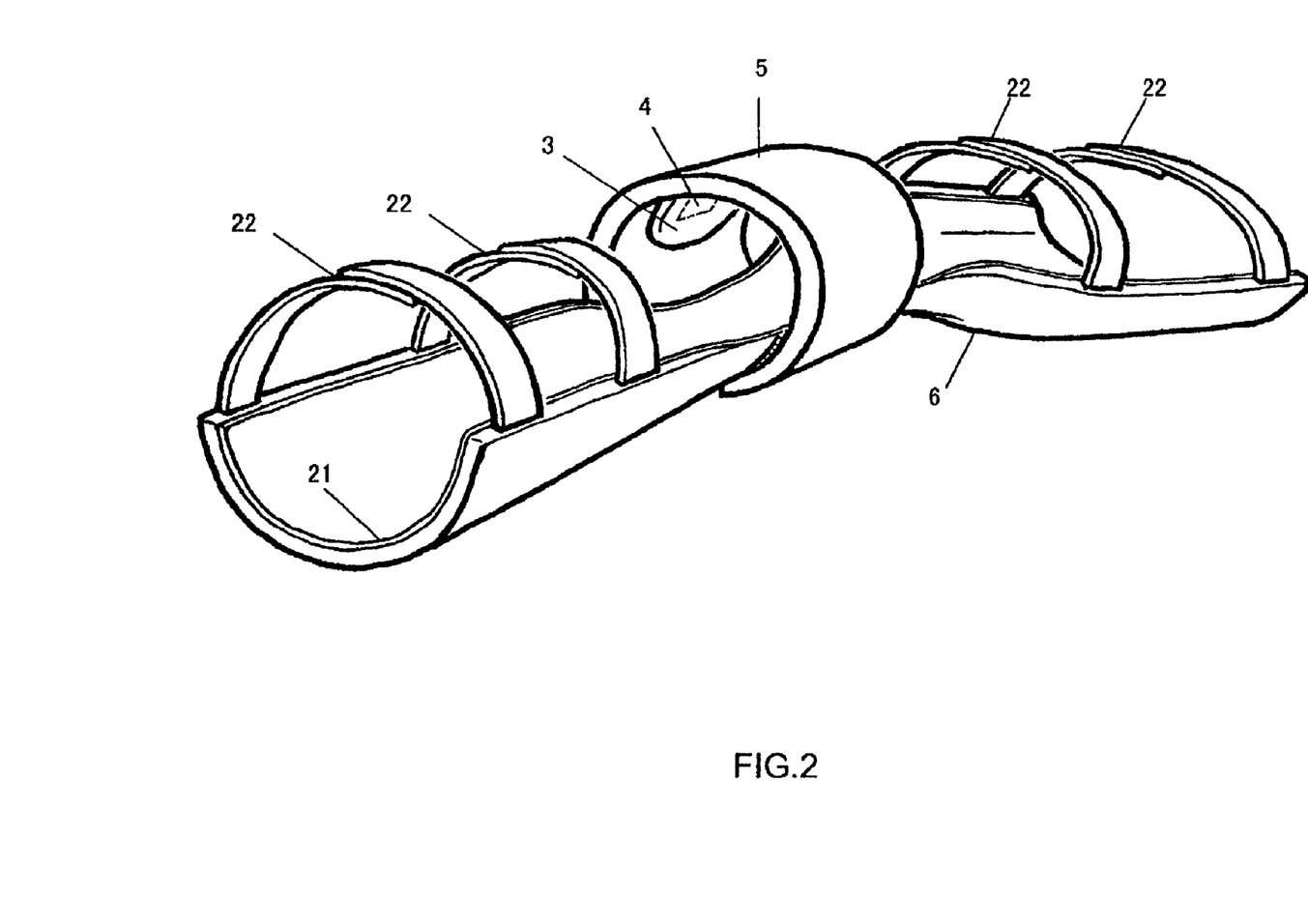
FIG. 2: the perspective view of the wrist detecting assembly of the first embodiment shown in FIG. 1.

This embodiment is to measure the blood pressure of the radial artery by applying the external pressure to the radial artery 7 and detecting radial arterial pulse in wrist. As shown in FIG. 2, the wrist detecting assembly 1 includes four parts: the pressure bladder 3, the arterial pulse transducer 4, the bladder holding strap 5, and the wrist holding bracket 6.

Figure 3:
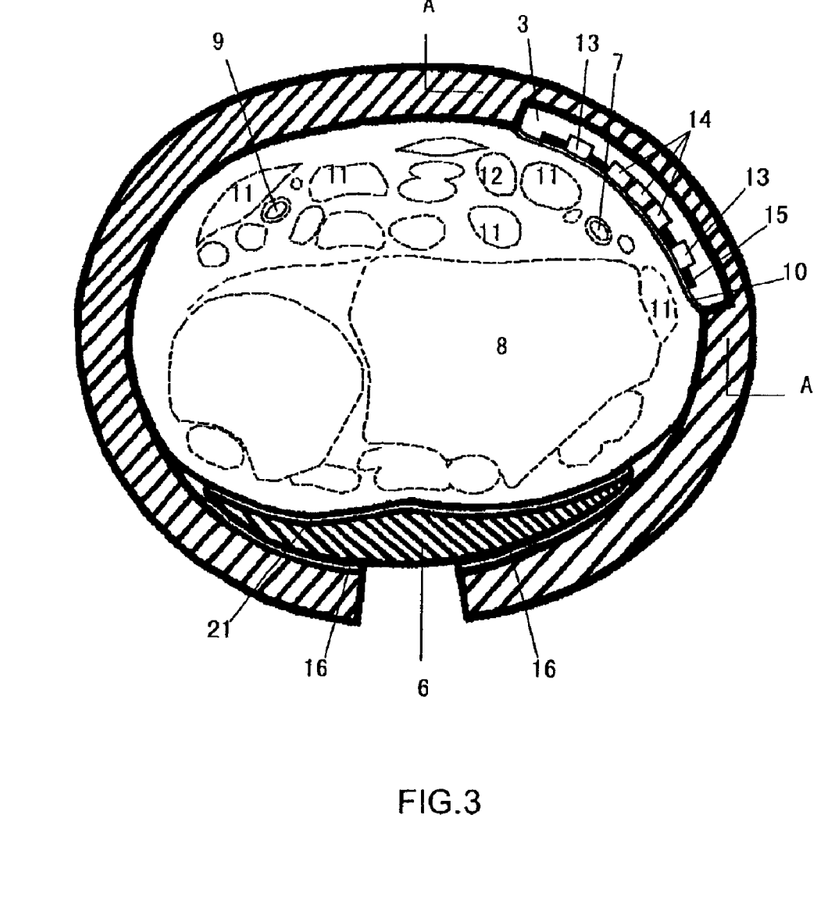
FIG. 3: the cross-section of the wrist detecting assembly as shown in FIG. 2.

As shown in FIG. 2 and FIG. 3, the radial artery pressure bladder 3 of this embodiment is a flat, round, air-filled bladder. In order to ensure that the bladder pressure can be sufficiently transmitted to the depth of the radial artery 7, on the one hand, the position of the bladder 3 should enable its center to armed to the radial artery 7 at the most protuberant spot on the volar aspect of the distal end of the radius; on the other hand, the diameter of the bladder 3 should be large enough. However, if the diameter is too large, the bladder 3 will press another ulnar artery 9 and some other vein synchronously, this diameter can be selected as between approximately ⅓ and ⅗ of the wrist diameter (e.g. about 30 mm for adult). In addition, to ensure that the bladder 3 won't produce circumferential tension within its walls due to inflation after the air is filled so as to effectively press the radial artery 7, the inner wall 10 of the bladder 3 which faces the wrist is made with transparent, resilient membrane shaped to upheave towards the wrist. The wall along the circumference and the outer wall of the bladder 3 are made of rigid material.

Figure 4:
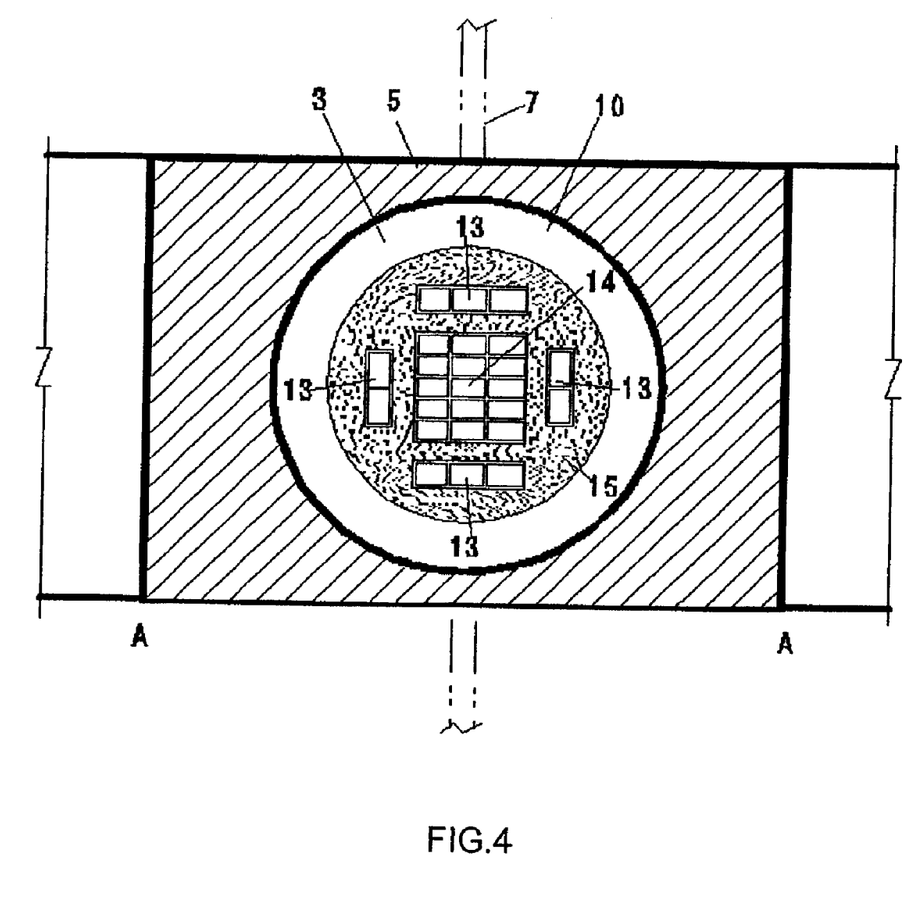
FIG. 4: the cross-sectional view of the arterial pulse transducer installed in the pressure bladder, along the A—A section of the wrist detecting assembly shown in FIG. 3.

Radial arterial pulse transducer 4 is an array of reflective photoelectric transducers. As shown in FIG. 3, there is a very complicated, nonhomogeneous structure inside the wrist. Take the area around the radial artery for instance, apart from the radius 8 bellow the artery 7, there are several tendons 11 and nerves 12 with high rigidity in the soft tissue on both sides of the radial artery, these tendons and nerves can block the pressure transmission in the soft tissue. According to the principles of mechanics, the site where the bladder pressure can be transmitted effectively to the radial artery 7 so as to accurately measure the blood pressure of the radial artery is the site near the skin and radius 8, but far from the tendons 11 and nerves 12. However, in fact, in the wrist (see FIG. 1, FIG. 3), the depth and position of the radial artery 7 itself, as well as the shape and position of the tendons 11 and radius 8, change with the position along the axial direction of the wrist. Especially the shape of the cross section of the radius 8 at the most protuberant spot on the volar aspect of the distal end of the radius is not regular and changes with different people. Obviously, to locate the above-mentioned site to accurately measure the blood pressure of the radial artery, a transducers array of 4 must be used to detecting the arterial pulse signals meticulously from many sites for comparison and analysis. In order to place the transducers 4 with the above-mentioned pressure bladder 3 onto the wrist while do not obstruct the bladder wall to evenly press the wrist, this transducer array 4 is mounted within the above-mentioned bladder 3. As shown in FIG. 4, in this embodiment, the transducer array 4 consists of ten infrared light emitting diodes 13 and fifteen phototransistors 14, among which the fifteen phototransistors 14 form a rectangle array. This array has three column phototransistors parallel to the radial artery 7, with each column consisting five row phototransistors. There is a clearance in between both the columns and in between the rows. The ten infrared light emitting diodes 13 are arranged around the four sides of the rectangle array, with clearance between the diodes and the four sides of the array. These emitting diodes 13 and phototransistors 14 are fixed to the inside of the inner wall 10, made of semi-transparent membrane, of the above-mentioned bladder 3. When fixing them, the light emitting surface of the emitting diodes 13 and the light receiving surface of the phototransistors 14 should face the inside of the inner membrane wall 10, and the center of the phototransistor array should point to the center of the inner membrane wall 10. In addition, to avoid the phototransistors 14 are affected by the light from the light emitting diodes 13 and the environment light, a layer of shading sheet 15 of good extensibility (black sponge sheet for instance) is glued between the light emitting diodes 13 and the phototransistor array, as well as around the whole phototransistor array. When detecting the pulse of the radial artery 7 with this phototransistor, the infrared light is emitted by the ten light emitting diodes 13 from ten different sites, passing the inner semi-transparent membrane wall 10, into the wrist. Because the intensity of the light reflected into the phototransistors 14 change along with the radial arterial volume caused by the periodical change of its blood pressure, so as to change the output current of the phototransistors 14, the volume change (pulse) of the radial artery 7 can be transformed into the fifteen channel of radial arterial pulse signals to output.

Bladder holding scrap 5 is used to hold the pressure bladder 3 installed the above-mentioned pulse transducer. To simplify the structure, this embodiment integrates the bladder 3 and the holding strap 5 into one wrist detecting assembly. This is done by using a strap with certain thickness and rigidity and, processing a flat, circular depression whose diameter is the same as the diameter at the bladder 3 on the wrist side of said strap in a position corresponding to radial artery, and then the edge of the inner bladder wall 10 is glued to the edge of the depression of strap 5 to form the above-mentioned bladder 3 by integrating the inner bladder wall 10 of membrane and the depression. In order to avoid the outer wall of the bladder moving towards the outside caused by bladder inflation, the strap 5 should be made with non-extensible material, and the apparatus for fixing its two ends should also be non-extensible. In this embodiment, the two ends of the strap 5 are fixed on the backside of the wrist holding bracket 6 with nylon agraffe 16. Meanwhile, to prevent the bladder 3 from moving along the circumference during the bladder inflation, the strap 5 (at least in the part surround the volar side of wrist from the dorsal side of the radius 8 to the volar side of the ulnar) should be rigid. This is because that the bladder moving along the circumference is due to mat the cross section of the wrist is a ellipse, and bladder 3 which is a local pressure bladder, is placed right on the connection of the arc of the two different curvatures. This will cause imbalance in the circumferential component of the pull force in the bladder holding strap 5 of the two sides of the bladder, so as to cause the bladder 3 to move along the circumference. In addition, the strap 5 should possess appreciably elasticity so that when the diameter of the wrist is reduced due to long-term, continuous pressure, its resilient capability can still enable the bladder 3 to wrap tightly onto the wrist without any movement. On the other hand, to guarantee that only the radial artery 7 to be measured is sufficiently pressured by bladder 3, and the pressure from the strap 5 to the wrist and other parts is reduced as much as possible, the effective area of the interface between the strap 5 and the wrist should be as big as possible. To do this, the strap width should be as wide as possible (larger than 50 mm for normal adults), and the side of the strap facing the wrist 18 and the hand 17 should be shaped to match with the irregular shape of dorsal side of the wrist and the hand.

Figure 5:
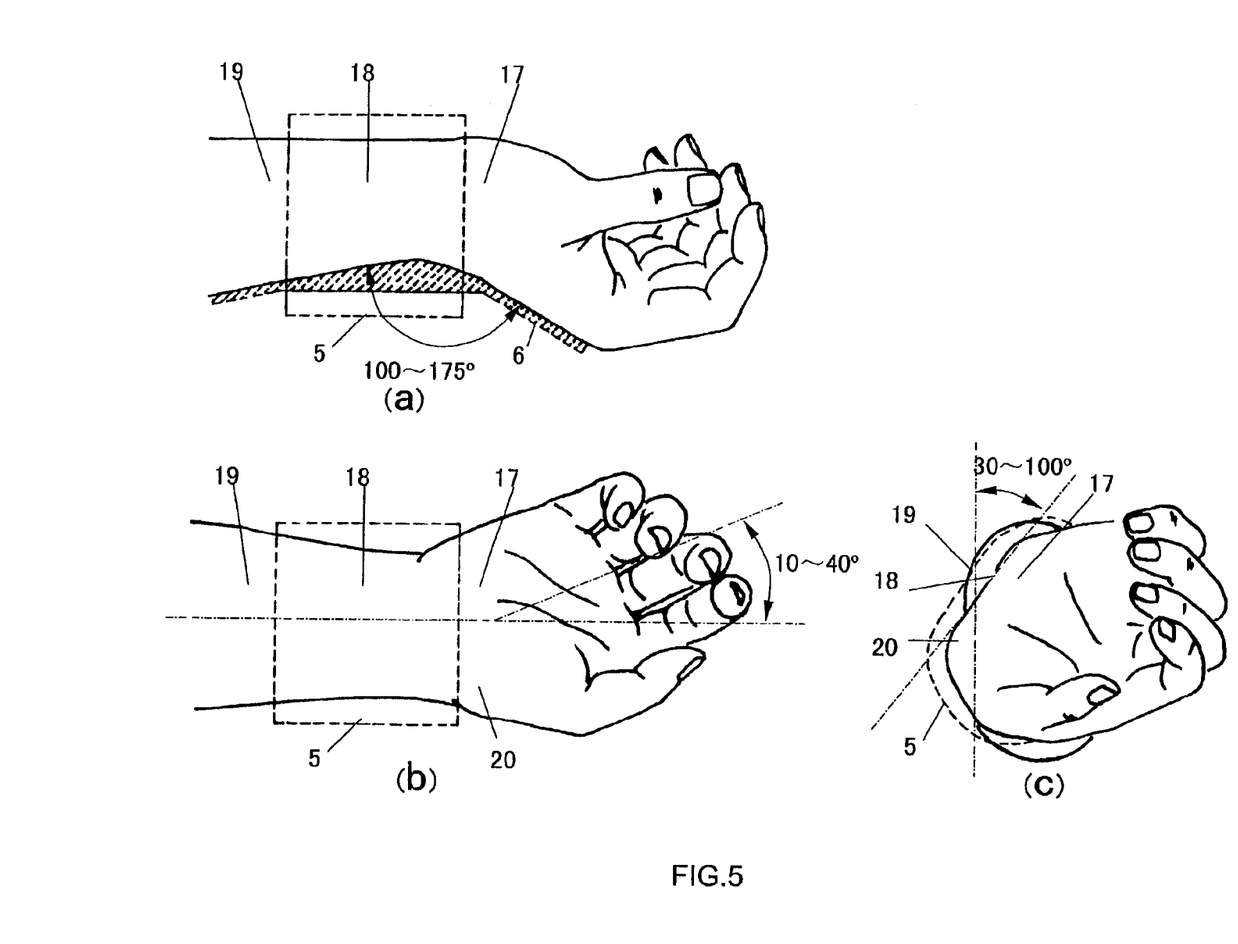
FIG. 5: the schematic illustration of the three angles between the wrist and the hand, formed by the wrist holding bracket of the wrist detecting assembly shown in FIG. 2.

The wrist holding bracket 6 is a curved board made of material with high rigidity. Its length and width should cover the entire back of the hand, the dorsal side of the wrist and the dorsal ado of the forearm near the elbow joint. The wrist holding bracket 6 has three functions. The first function is to keep the posture of the wrist 18 to the most suitable posture for measuring the blood pressure of the radial artery. At the same time, it limits the turning of the wrist 18 and the bending of the hand 17 so that when the subject moves, the position of the pressure bladder 3 and the pulse transducer 4, as well as the tendon 11, nerves 12, and radius 8 in the wrist in relative to the radial artery 7 stays the same. As shown in FIG. 5(a) and FIG. 5(c), the shape of the wrist holding bracket 6 should make the angle between the dorsal side of the wrist 18 and the dorsal side of the hand 17 to be an angle between approximately 100 and 170 degrees, and make the turning angle of the wrist 18 relative to the forearm 19 to be an angle between approximately 30 and 100 degrees towards the medial side of body, and also make the deflecting angle from the central line of the hand 17 in relative to the central line of the volar side of the wrist 18 at between approximately 10 and 40 degrees towards the little finger. In which, to make the hand to deflect slightly towards the little finger can extend the area between the protuberant spot of the hand 20 bellow the thumb and optimal site so that the wide bladder holding strap can close up the wrist. The second function of the wrist holding bracket 6 is to improve the stability of the bladder holding strap 5. Considering that the reason of the bladder 3 moving in the direction of the wrist's long axis towards the hand during the bladder inflation is that the diameter of the middle part of the forearm 19 is larger than the that of the wrist joint section 17 so that the component of forces towards the hand 17 is produced on the outer wall of the bladder 3 during bladder pressure, therefore, as shown in FIG. 5(a), the thickness of the holder 6 in the part connecting the dorsal side of the hand 17 and the dorsal side of the wrist 18 should be increased, so as to eliminate the difference between the diameters of the wrist joint section 17 and middle part of the forearm 19. In addition, the increase in thickness in the connecting part of the wrist holding bracket can also increase the intensity when the holder is used to hold the hand 17. Moreover, the sinking surface of the dorsal side of wrist joint part due to the hand bending towards the dorsal side is filled to a regular column surface. The third function of the wrist holding bracket 6 is to disperse the pressure of the bladder holding strap 5 on the dorsal side of the wrist. For this reason, the inside of the wrist holding 9 bracket 6 should be shaped to matches well with the irregular shape of the dorsal side of the wrist 18, and it is preferred to prepare several kinds of holders for different shapes and widths of the wrist. Also, to avoid causing discomfort to the subject a thin layer of soft cushion 21 should be glued to the inner side of the holder 6. In addition, to tie the subject's hand 17, the wrist 18, and the forearm 19 inside the wrist holding bracket, several small straps with nylon agraffes at the ends should be fixed onto the wrist holding bracket 6.

In this embodiment, the pressure feeding-measuring system 2 includes a pressure feeding device and a signal processing device. The pressure feeding device includes voltage/pressure converter 24, bladder pressure setting circuit 27; the signal processing device includes amplifier and filter 23, optimal site selector 28, pulse amplitude detecting circuit 29, pressure transducer 25, pressure signal amplifier 26, pressure value output circuit 30, diastolic blood pressure calculator 31 and optimal site warning circuit 38.

The operational process of the apparatus for non-invasive intermittent measurement of the radial artery blood pressure in this embodiment is:

As shown in FIG. 1, the fifteen outputs of the pulse transducer array 4 of the wrist detecting assembly 1 are connected separately with the fifteen inputs of the multi-channels of amplifier and filter 23 At the same time, the air tubing of the radial arterial pressure bladder 3 is connected to the pressure output of the voltage/pressure converter 24 of the pressure feeding-measuring system 2, and the pressure input of the pressure transducer 25, which is connected to the pressure signal amplifier 26.

When setting the wrist detecting assembly, first, the hand 17, wrist 18 and forearm 19 of subject are fixed into the wrist holding bracket 6 of the wrist detecting assembly 1. Then, after pointing the center of the bladder 3 of the wrist detecting assembly 1 directly to the radial artery 7 on the most protuberant spot on the volar aspect of the distal end of the radius, wrap the bladder holding strap 5 to the wrist 18. Lastly, fix the two ends of the holding strap to the wrist holding bracket 6 with nylon agraffes 16.

When the blood pressure measurement begins, the bladder pressure setting circuit 27 of the pressure feeding-measuring system 2 starts to adjust automatically the input voltage of the voltage/pressure converter 24, so as to inflate the bladder 3 of the wrist detecting assembly 1 to apply the external pressure to the radial artery 7. Meanwhile, the pulse transducer array 4 of the wrist detecting assembly 1 detects the radial arterial pulse signals. These pulse signals are fed to the pulse signal processing device 1 to amplify and filter them, and then are fed to the optimal site selector 28 to find easily the optimal site to most accurately measure the blood pressure of the radial artery.

The selected optimal pulse signal is fed to a pulse amplitude detecting circuit 29 to find the maximum and the disappearance of their oscillation amplitude. According to the principles of the oscillometric method, the bladder pressure corresponding to the maximum and appearance of the oscillation amplitude will respectively equal the mean blood pressure and the systolic blood pressure of the artery to be measured. Therefore, when the maximum and disappearance of oscillation amplitude is found by the amplitude detecting circuit 29, a control signal is given so that the bladder pressure at the above-mentioned two moments are measured and are output by a pressure value output circuit 30; thus, the measured results of the mean blood pressure and the systolic pressure are obtained, and the diastolic blood pressure can be obtained by the diastolic blood pressure calculator 31.

On the other hand, for the convenience for the location of the pressure bladder, the selected optimal pulse signal is also used for controlling a transducer position display. This display can indicate the exact position of the transducer measured the optimal pulse signal in the transducer array in the most visual way (for example, drawing the transducer array) on the display screen. When setting the bladder 3, the position of the bladder 3 is adjusted according to the display so that the transducer detected the optimal pulse signal is positioned in the center of the transducer array. In this embodiment, there is also an optimal site warning circuit 38. When setting the bladder or during long-term measurement of the blood pressure, if the subject's wrist turns significantly (even though the wrist holding bracket 6 can limit the turning of the wrist 18 in relative to the forearm 19, the wrist can still turn to a certain extent) so that if the transducer is too far from the center of the transducer array, the transducer position warning circuit 38 will give warning signal to remind the operator to readjust the position of the pressure bladder 3. Since the optimal pulse signal is selected in every measurement, it is ensured that the measurement is done at the optimal site every time.

This embodiment is especially suitable for clinic or family monitoring of long-term blood pressure of the patient whose blood pressure changes very smoothly (for example, after a surgery, or recovering from a treatment).

The Second Embodiment

Figure 7:
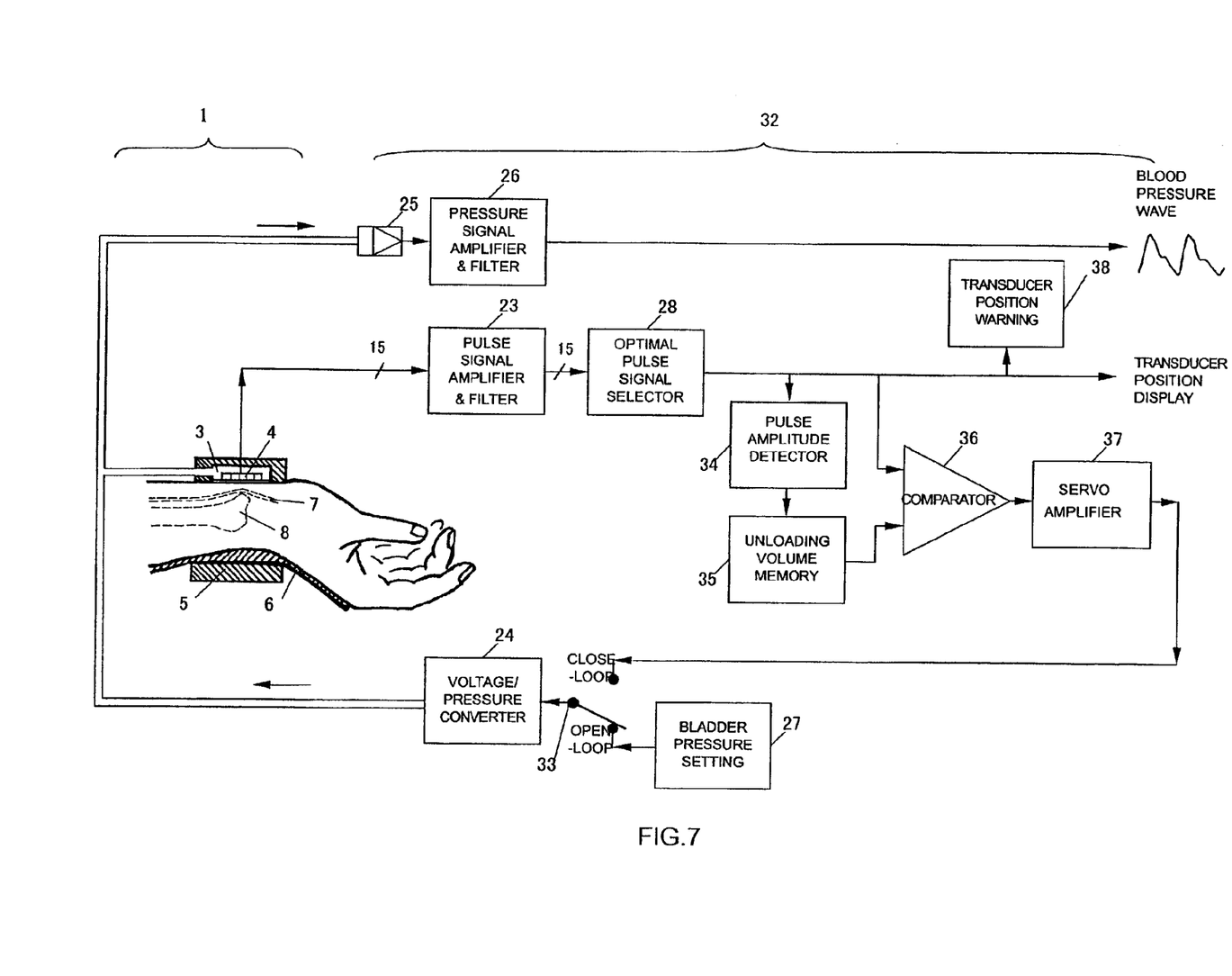
FIG. 7: the simplified block diagram of the second embodiment of this invention.

The second embodiment of this invention is a method and an apparatus for non-invasive continuous measurement of radial artery blood pressure on the wrist with the vascular unloading method. As shown in FIG. 7, the wrist position method and the optimal pulse selecting method in this embodiment are both the same as those used in the first embodiment. Their main difference is that the selected optimal pulse signal is used for non-invasive continuous measurement of the radial artery blood pressure wave with the vascular unloading method. Since the vascular unloading method is a known technique, its operation process will be described in detail later.

The apparatus of this embodiment is shown in FIG. 7. The pulse signal processing device 1 can be the same as those used in the first embodiment. The wrist holding bracket and bladder holding strap is also the same as in the first embodiment, so it won't be repeated here. In this embodiment, the main difference from the first embodiment is that the output of the optimal site selector 28 of the pressure feeding-measuring system 32 is not used to control the pressure value output circuit to read the pressure of the bladder 3, but is connected with the input of the voltage/pressure converter, through a comparator and a servo amplifier, to form a closed-loop feedback control system to control the pressure change of the bladder 3.

Figure 8:
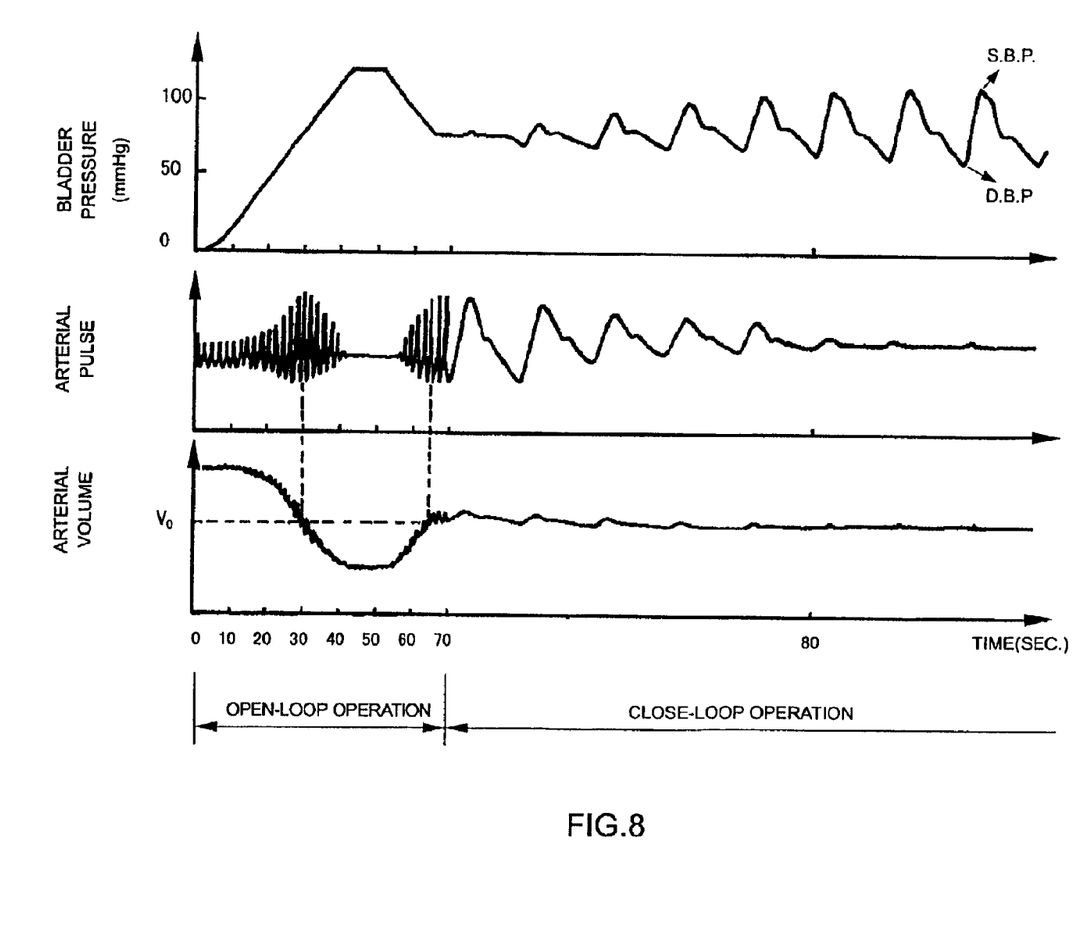
FIG. 8: the schematic illustration of the method for measuring the blood pressure wave of the second embodiment.

Before continuous measuring the blood pressure with this method and apparatus, in order to find and memorize the volume of the radial artery 7 at its unloading state, the pressure feeding-measuring system 2 first turns the operational state switch to the "open-loop". As shown in FIG. 8, under the open-loop operational state, like the oscillometric method, the bladder pressure setting circuit 27 automatically adjusts the voltage feed to the voltage/pressure converter so that the bladder 3 will start the pressure to radial artery 7. At the same time, the pulse signals of the radial artery 7 are detected by the pulse transducer array 4 from fifteen sites of the wrist, and are amplified, filtered, then are fed to the optimal site selector 28. The selected optimal pulse signal is fed to the amplitude detecting circuit 34. When the maximum oscillation amplitude is detected, i.e. when it has been identified that the radial artery 7 is already pulsating around its unloading volume, along with the periodical change of the inner blood pressure, the system stops the bladder pressure setting circuit 27 from adjusting the pressure of the bladder 3, and enable the unloading volume memory 35 to memorize the average of the radial artery pulse wave (D.C. component of the pulse signal) as the unloading volume Vo of subject's radial artery.

Then, the pressure feeding-measuring system 32 automatically turns the operational state switch to the "close-loop", by a comparing circuit 36, the pulse signal near the unloading volume of the radial artery 7 detected by the pulse transducer is subtracted from the unloading volume Vo memorized by the unloading volume memory 35. The gain of the servo amplifier 37 is increased steadily, so that the obtained difference (e.g. the pulsation of the radial artery pulse wave) is amplified and phase compensated, and fed to the voltage/pressure converter 24 to control the pressure of bladder 3 to apply further the external pressure whose wave is the same as the blood pressure wave to radial artery 7, so that the amplitude of the radial arterial pulse is reduced, as shown in the beginning section of the close-loop state in FIG. 8 (to view easily, the waves in the close-loop state is extended along the time axis). Obviously, when the gain of the servo amplifier 37 is adjusted to where the bladder pressure to the radial artery 7 is completely the same as the blood pressure wave of the radial artery not only in the shape but also in the amplitude, i.e. when the force on both the inside and outside of the vessel wall of the radial artery 7 is made to reach a dynamic balance, as shown in the section after the close-loop state in FIG. 8, the vessel wall of the radial artery 7 will not pulsate with the periodical change of the blood pressure, and the blood vessel volume will be maintained on the unloading volume Vo. Therefore, under the close-loop operation state, if the moment when the pulse amplitude of the radial artery 7 become to near zero is fund during steadily increasing the gain of the servo amplifier 37, it is assured that from the moment, the pressure in the pressure bladder 3 will equal the blood pressure of the radial artery 7 at any time. Thus, the non-invasive continuous measurement of the radial artery blood pressure wave is obtained by measuring continuously the pressure of the pressure bladder 3 with a pressure transducer 25 that is connected to the pressure bladder 3.

This embodiment is especially suitable for the clinical monitoring of the patients whose blood pressure changes very fast so as to need long-term, continuous measurement of beat-by-beat blood pressure (for example, patients under anesthesia, surgery, or emergent care).

The Third Embodiment

Figure 10:
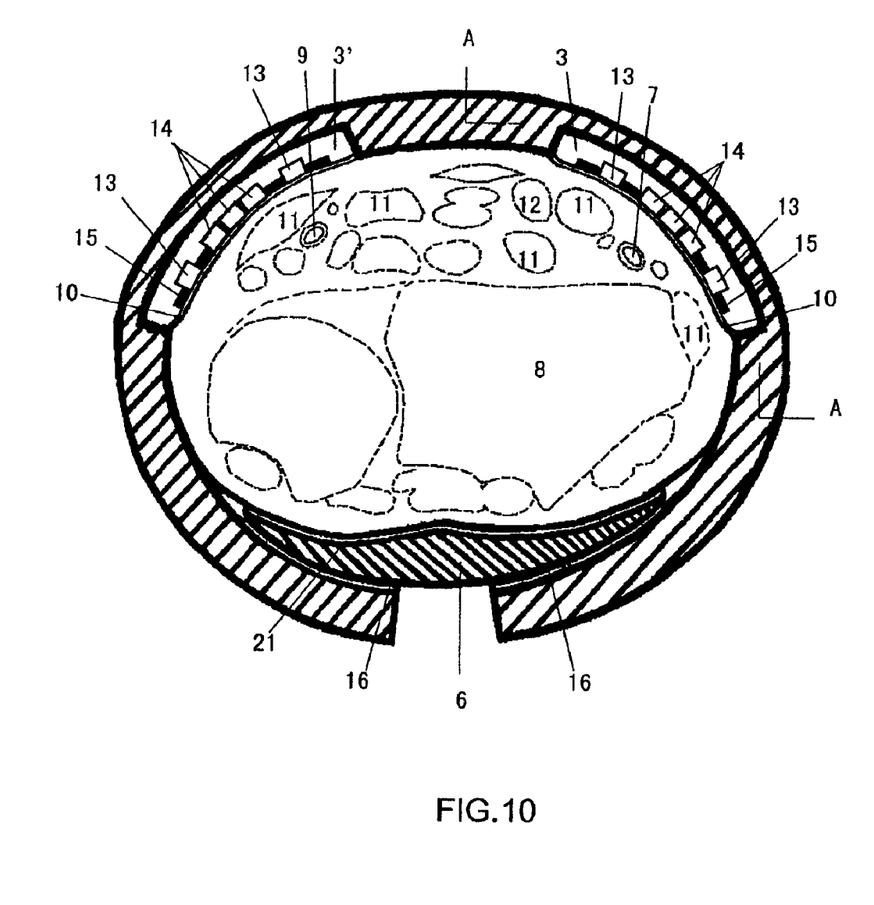
FIG. 10: the cross-section of the wrist detecting assembly of the forth embodiment of this invention.

This embodiment is a method and a apparatus for both intermittent measurement of blood pressure and continuous measurement of the blood pressure wave on the radial artery of wrist, as shown in FIG. 10. In this embodiment, the wrist position method and the optimal site selecting method are both the same as in the first embodiment. Their main difference is that the selected optimal pulse signals are used exchangeablely for non-invasive measurement of the mean and the systolic blood pressure with the oscillometric method and non-invasive measurement of the continuous blood pressure wave with the vascular unloading method.

Figure 9:
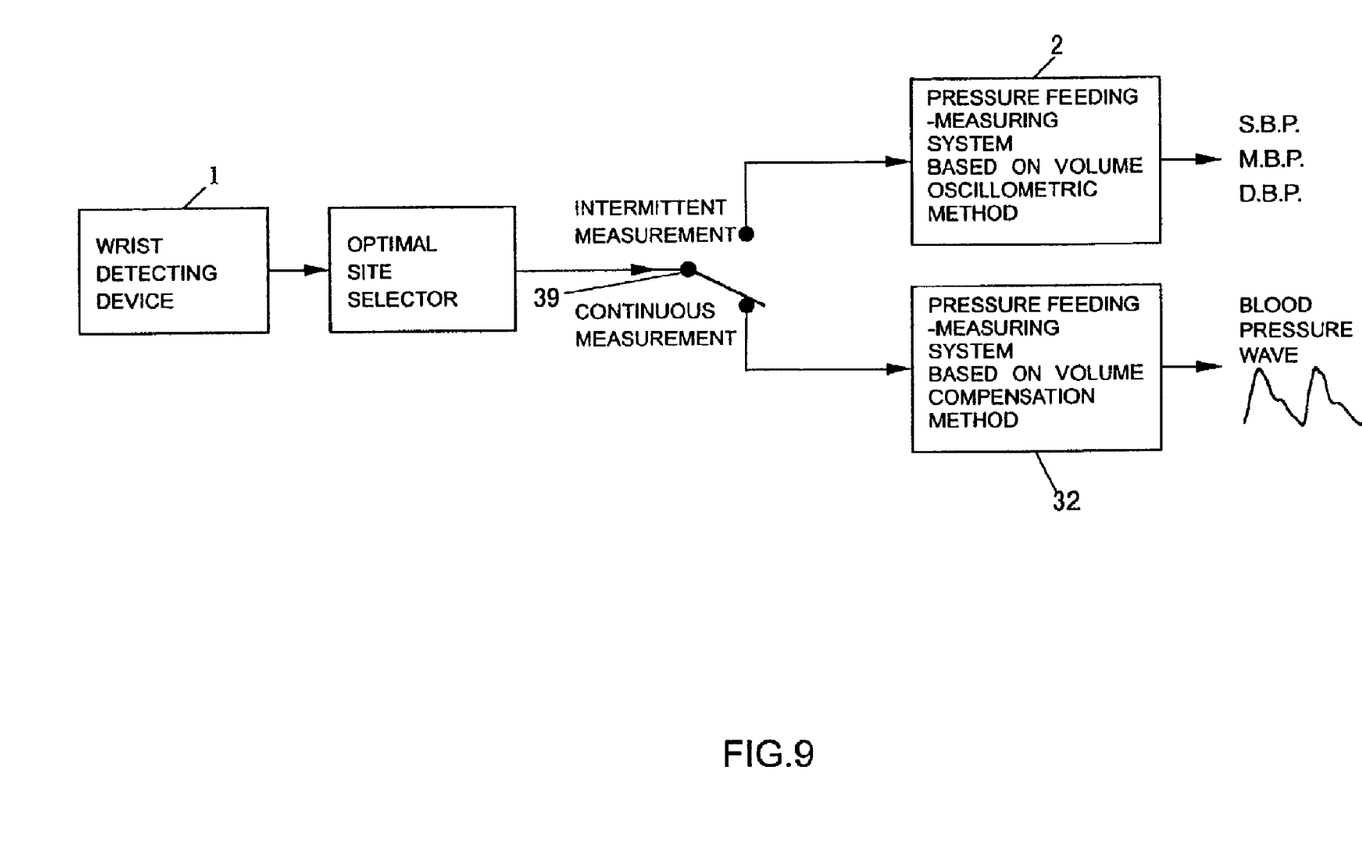
FIG. 9: the simplified block diagram of the third embodiment of this invention.

The apparatus of this embodiment also comprises a wrist detecting assembly 1 and a pressure feeding-measuring system 2. Most parts of the wrist detecting assembly and the pressure feeding-measuring system are the same as the above two embodiments. The difference is that, in order to both measure intermittently the blood pressure and measure continuously the blood pressure wave, as shown in FIG. 9, the pressure feeding-measuring system (parts 29, 30, 31 for controlling and reading the bladder pressure in FIG. 1) of the first embodiment and the pressure feeding-measuring system (parts 34, 35, 36, and 37 for controlling the bladder pressure change in FIG. 7) of the second embodiment are exchanged through a "intermittent measurement-continuous measurement" function switching device 39. Since this switch is simple, it won't be further discussed here.

For patients whose blood pressure changes sometimes smoothly and sometimes fast, this embodiment can make it possible to choose freely the measuring intervals in a range from zero to infinity according to the patient's conditions for long-term monitoring of the blood pressure in clinic and family.

The Forth Embodiment

The forth embodiment of this invention is the intermittent and/or continuous measurement of the blood pressure alternately on radial artery 7 and ulnar artery 9. The wrist position method and optimal site selecting method are both the same as the above three embodiments. The main difference is that there are two pressure bladder, i.e. bladder 3 and bladder 3', which are placed separately on radial artery 7 and ulnar artery 9 to measure blood pressure alternately.

As shown in FIG. 10, the position of ulnar artery 9 is considerably deep, and there are tendons 11 in between ulnar artery and skin, so the bladder pressure cannot be sufficiently transmitted to the ulnar artery 9; therefore, it is difficult to accurately measure the blood pressure of the ulnar artery on any site of wrist. Usually, for a given wrist, the radial artery blood pressure is the same as the blood pressure of ulnar artery, and if the wrist does not turn too much, the difference between the pressure in the ulnar artery pressure bladder 3' and the pressure transmitted to the ulnar artery 9 is constant. Therefore, the result of the blood pressure measurement on the radial artery can be used as standard to calibrate the result of the blood pressure measurement on the ulnar artery.

For example, calculating the difference (Di) between the mean blood pressure measured from the radial artery 7 and the bladder pressure of ulnar artery 9 corresponding to the maximum pulse amplitude of ulnar arterial pulse, and calculating the ratio (Pi) of the ulnar arterial pulse amplitude to the maximum amplitude of the ulnar arterial pulse when the bladder pressure of ulnar artery is equal to the systolic blood pressure measured from the radial artery; so that, each time thereafter, the new mean blood pressure of ulnar artery can be obtained by subtracting Di from the bladder pressure of ulnar artery corresponding the maximum amplitude of measured ulnar arterial pulse, and the new systolic blood pressure of ulnar artery can also be obtained by measuring the bladder pressure of ulnar artery when the ulnar arterial pulse amplitude with the Pi ratio to its maximum amplitude during the bladder pressure of ulnar artery is higher than the new mean blood pressure of ulnar artery.

During long-term, continuous measurement of the blood pressure with the method of this embodiment, to avoid the change in Di and Pi due to too much turning of the subject's wrist, Di and Pi should be recalculated according above-mentioned method automatically and periodically.

To apply the methods of this embodiment, the apparatus used by this embodiment also comprises a wrist detecting assembly 1 which basically the same as in the first embodiment, Also, it can use any of the two independent pressure feeding-measuring systems used in the above three embodiments. But as shown in FIG. 10, a pressure bladder 3' to press the ulnar artery is placed opposite to the existing radial artery pressure bladder 3 on the bladder holding strap 5, and also a pulse transducer for detecting the ulnar artery pulsation is installed in the bladder 3'.

In this embodiment, the radial artery pressure bladder and the radial arterial pulse transducer should have the same structure as that used in the first embodiment so as to accurately measure the blood pressure of the radial artery like the first embodiment. Ulnar artery pressure bladder 3' can be the same structure as in the first embodiment, but the ulnar arterial pulse transducer does not need to use a photoelectric sensor array as complicated as the radial arterial pulse transducer. This is because, However, to find the ulnar artery conveniently, it is preferred to place more than two photoelectric sensors of parallel-connection along the circumference of the wrist over the ulnar artery, so that, when applying the photoelectric sensors of parallel connection, only one channel amplifier and filter for the ulnar arterial pulse signals is required, and the optimal site selector can be omitted.

Since pain and numbness caused by long-term, continuous pressure on one site can be avoided by the use of two arteries alternately, this embodiment can prolong considerably the time for repeated and continuous blood pressure measurement.

The Fifth Embodiment

In above embodiments, photoelectric device array, placed on the wrist skin near the radial artery, are used to detect the radial arterial pulse signal from many site to find the optimal measuring site and to obtain the optimal pulse signal, so as to measure the blood pressure of radial artery accurately and easily. In this embodiment, in order to simplify the instrument, one photoelectric device, or several parallel-connection photoelectric devices is used to detect the radial arterial pulse signal from one site on the wrist. In this embodiment, photoelectric device and light emitting device are arranged along the direction vertical to the radial artery with the distance above between approximately 3 mm and 10 mm. The midpoint of two kinds of devices corresponds to the center of said bladder wall, and the two kinds of devices are fixed on the inside of the wall of said pressure bladder which closes to the wrist.

Obviously, these photoelectric devices output one channel of arterial pulse signal. In this embodiment, the optimal site selector is not necessary.

The Sixth Embodiment

In this embodiment, an arterial volume transducer for detecting the arterial pulse signal can be placed on the site near the artery to be measured. In fact, there are many kind of sensors that can be used to directly or indirectly detect the arterial pulse signal. In this embodiment, a pressure transducer is used to detect the pulse signal of a radial artery. The pressure-sensing surface of the pressure transducer is connected to a pressure bladder positioned on the skin above the radial artery by air or liquid. Because the pulsation of radial artery can cause an oscillation in bladder pressure, using the pressure transducer to measure the bladder pressure and getting out the oscillation component of the bladder pressure can be used to obtain the pulse signal of the radial artery. The pressure transducer can be placed either in the inside of pressure bladder, or in the place where away from the wrist to be measured. In this case, the optimal site selector is also not necessary. It should be noted that in this arrangement, the arterial pulse signal is not detected from one site of wrist, but from some general area covered with whole pressure bladder.

The above embodiments are described only for illustrating this invention, but not for limiting this invention. This invention can also have many other embodiments and improvement plans. For example, in the above four embodiments, we used the oscillometric method for intermittent blood pressure measurement and the vascular unloading method for continuous blood pressure measurement. In both, the fact of whether or not the subject's arterial pulse oscillation amplitude reaches the maximum is used as the criterion to judge if the subject's artery blood pressure is at its unloading state, air pressure control is used to control the external pressure on the artery to be measured. In fact, other criterions, such as the shape of the pulse waveform or the change in the level of the base line, the change in the oscillation amplitude of the small vibration wave added artificially to the pulse wave, and the change in the speed of blood flow in the artery being measured, can be used to judge the unloading state of the subject's artery. In addition, hydraulic pressure control can also be used to control the external pressure on the subject's artery.

What is claimed is:

1. A method for non-invasively measuring arterial blood pressure at a wrist of a patient, said method comprising the steps of:
    a) keeping a wrist of a patient at a posture which lowers a position of at least one tendon of the wrist near to a radial artery to be measured, and causes the radial artery to be close to a radius of the wrist;
    b) applying a changing external pressure to the skin above a point where the radial artery crosses a most protuberant spot on a volar aspect of the radius of the wrist;
    c) detecting a pulse wave signal of the radial artery along with a change in said external pressure on the skin above said point;
    d) measuring blood pressure of the radial artery by measuring said external pressure applied to the radial artery when said pulse wave signal changes.

2. The method as defined in claim 1, wherein said step of keeping the wrist at said posture comprises forming a flexing angle of between approximately 100 and 170 degrees between a dorsal side of the wrist and a dorsal side of the hand attached to the wrist.

3. The method as defined in claim 1, wherein said step of keeping the wrist at said posture comprises forming a flexing angle of between approximately 100 and 170 degrees between a dorsal side of the wrist and a dorsal side of the hand attached to the wrist, and synchronously forming a turning angle of the wrist relative to the forearm attached to the wrist of between approximately 30 and 100 degrees towards a medial side of the patient's body.

4. The method as defined in claim 1, wherein said step of keeping the wrist at said posture comprises forming a flexing angle of between approximately 100 and 170 degrees between a dorsal side of the wrist and a dorsal side of the hand attached to the wrist, and synchronously forming a deflecting angle from a central line of the palm of the hand relative to a central line of a volar side of the wrist at between approximately 10 and 40 degrees towards the little finger of the hand.

5. The method as defined in claim 1, wherein said step of keeping the wrist at said posture comprises forming a flexing angle of between approximately 100 and 170 degrees between a dorsal side of the wrist and a dorsal side of the hand attached to the wrist, and synchronously forming a turning angle of the wrist relative to the forearm attached to the wrist of between approximately 30 and 100 degrees towards a medial side of the patient's body and a deflecting angle from a central line of the palm of the hand relative to a central line of a volar side of the wrist at between approximately 10 and 40 degrees towards the little finger of the hand.

6. The method as defined in claim 1, wherein said step of detecting a pulse wave signal of the radial artery includes measuring an oscillation in said external pressure caused by a pulsation of the radial artery.

7. The method as defined in claim 1, wherein said step of detecting a pulse wave signal of the radial artery includes measuring an oscillation in volume of the radial artery at a site which is on the skin above the radial artery and within a compressing area of said external pressure.

8. The method as defined in claim 1, wherein said step of detecting a pulse wave signal of the radial artery includes measuring an oscillation in volume of the radial artery at a plurality of sites which are on the skin above the radial artery and within a compressing area of said external pressure, and selecting one optimal measuring site, and then outputting the volume oscillation measured at said optimal measuring site as an optimal pulse wave signal, said plurality of sites including at least two columns and two lines of measuring sites along directions that are parallel and perpendicular to the radial artery respectively.

9. The method as defined in claim 8, wherein said step of selecting one optimal measuring site comprising the steps of:
   a) selecting a column of measuring sites from all columns of measuring sites, said selected column of measuring sites having a feature that the pulse wave signals detected at said selected column of measuring sites all possess maximum amplitude points when said external pressure is close to the mean blood pressure of the patient, and amplitude values of the maximum amplitude points of the pulse wave signals detected at said selected column of measuring sites being larger than those detected at other columns of measuring sites;
   b) selecting one optimal site from the selected column of measuring sites, said optimal site having a feature that the pulse wave signal detected at said selected site possesses a point close to disappearance when said external pressure is close to the systolic blood pressure of the patient;
   wherein the value of the external pressure, when the amplitude of the pulse wave signals detected at said optimal site is close to maximum, and the value of the external pressure, when the amplitude of the pulse wave signal detected at said optimal site is close to disappearance, are lower than said values of external pressures detected at other sites of the selected column of measuring sites.

10. The method as defined in claim 8, further comprising displaying a position of said optimal measuring site within the compressing area of said external pressure, so that an operator can adjust a position of said external pressure according to said displaying step to cause a center of said external pressure to correspond to said optimal measuring site.

11. The method as defined in claim 8, further comprising the step of automatically checking whether the center of said external pressure corresponds to said optimal measuring site, and giving a warning signal when the center of said external pressure does not correspond to said optimal measuring site, so as to prompt an operator to readjust the position of said external pressure.

12. The method as defined in claim 1, wherein said step of measuring the blood pressure of the radial artery includes intermittently measuring the blood pressure of the radial artery according to an oscillometric method.

13. The method as defined in claim 1, wherein said step of measuring the blood pressure of the radial artery includes continuously measuring the blood pressure of the radial artery according to vascular unloading method.

14. The method as defined in claim 1, wherein said step of measuring the blood pressure of the radial artery includes at least one of intermittently measuring the blood pressure of the radial artery according to oscillometric method and continuously measuring the blood pressure of the radial artery according to vascular unloading method.

15. The method as defined in claim 1, wherein said step of applying changing external pressure to the radial artery, and detecting the pulse wave signal of the radial artery so as to measure the blood pressure of the radial artery can be switched to become applying changing external pressure to an ulnar artery of the wrist, and detecting the pulse wave signal of the ulnar artery so as to measure a blood pressure of the ulnar artery.

16. The method as defined in claim 15, further comprising the step of calibrating the measured ulnar artery blood pressure according to the measured radial artery blood pressure.

17. An apparatus for non-invasively measuring arterial blood pressure at a wrist of a patient comprising:
   a) a wrist holding device including a support board, wherein said support board is shaped to adapt to a flexing angle of between approximately 100 and 170 degrees between a dorsal side of the wrist and a dorsal side of a hand attached to the wrist and a turning angle of between approximately 30 and 100 degrees of the wrist relative to the forearm attached to the wrist towards a medial side of the patient's body;
   b) a pressure bladder for applying an external pressure to the radial artery, wherein said pressure bladder comprises a compressing wall adapted to face the skin above the radial artery of the wrist;
   c) a pressure bladder holding device for stably positioning said pressure bladder on the skin above a point where the radial artery crosses a most protuberant spot on a volar aspect of the radius of the wrist;
   d) a pulse transducer for detecting a pulse wave signal of the radial artery; and
   e) a pressure feeding-measuring system connected to said pressure bladder and said pulse transducer; said pressure feeding-measuring system including a pressure feeding device for feeding pressure to said pressure bladder, and a signal processing device for processing the detected pulse wave signal of the radial artery and controlling said pressure feeding device, so as to measure blood pressure of the radial artery by measuring said external pressure applied to the radial artery when the detected pulse wave signal of the radial artery changes.

18. The apparatus as defined in claim 17, wherein said support board is made of a rigid material and possesses a shape adapted to cover at least a portion of the dorsal side of the hand, the flexing wrist joint, and the forearm attached to the wrist, and has several straps fixed onto the support board by several non-extensible devices respectively for stably holding the forearm, wrist and hand of the patient to the support board.

19. The apparatus as defined in claim 17, wherein said support board is shaped to further adapt to a deflecting angle from a control line of the palm of the hand relative to a central line of the volar side of the wrist at between approximately 10 and 40 degrees towards the little finger of the hand.

20. The apparatus as defined in claim 18, wherein said support board comprises an inner surface adapted to face the skin of the wrist and an outer surface opposite to said inner surface, said inner surface is shaped to adept to at least the shape of the irregular surface of the dorsal side of the flexing wrist joint, and a potion of said outer surface is adapted to cover at least the dorsal side of the flexing joint and is shaped to regular column surface.

21. The apparatus as defined in claim 17, wherein said pressure bladder and said bladder holding device are integrated into a whole, to form a strap embedded with said pressure bladder, said compressing wall of said pressure bladder is made of a resilient membrane shaped to upheave towards the wrist, said strap is made of at least a semi-rigid material with slight elasticity and shaped into a ring with an elliptic cross section similar to that of the wrist, and two ends of an opening of said strap are connected by non-extensible means.

22. The apparatus as defined in claim 17, wherein said pulse transducer is a pressure transducer having a pressure sensing surface connected to said pressure bladder by at least one of air and liquid.

23. The apparatus as defined in claim 17, wherein said pulse transducer is a volume transducer; said volume transducer is preferably a reflective photoelectric transducer that consists of at least one light emitting device and at least one photoelectric device, said light emitting device and said photoelectric device are arranged vertical to the radial artery, wherein a midpoint between said at least one light emitting device and said at least one photoelectric device corresponds to an area center of said compressing wall of said pressure bladder, and said at least one light emitting device and said at least one photoelectric device are fixed on an inner surface of said compressing wall of said pressure bladder.

24. The apparatus as defined in claim 17, wherein said pulse transducer is a volume transducer array including a reflective photoelectric transducer array having a plurality of light emitting devices and a plurality of photoelectric devices which output independent pulse signals respectively; said photoelectric devices are arranged to form a rectangular array having at least two photoelectric devices in each of a line and a column of the array; said light emitting devices are arranged around said photoelectric device array; a center of said photoelectric device array corresponds to an area center of said compressing wall of said pressure bladder; said light emitting devices and photoelectric devices are fixed on an inner surface of said compressing wall of said pressure bladder; each output of the photoelectric devices of said photoelectric device array are respectively connected to corresponding input of an optimal transducer selector to select an optimal transducer.

25. The apparatus as defined in claim 24, wherein said optimal transducer selector selects the optimal transducer according to the steps of:

a) selecting one column of transducers from all columns of transducers, said selected column of transducers having a feature that the pulse wave signals detected by said selected column of transducers all possess maximum amplitude points when said bladder pressure is close to mean blood pressure of the patient, and amplitude values of the maximum amplitude points of the pulse wave signals detected by said selected column of transducers being larger than those detected by other columns of transducers;

b) selecting one optimal transducer from said selected column of transducers, said optimal transducer having a feature that the pulse wave signals detected by said optimal transducer possesses a point close to disappearance when said bladder pressure is close to systolic blood pressure of the patient, when the values of the bladder pressures when the amplitude of the pulse wave signals detected by said optimal transducer are respectively close to maximum and disappearance are respectively lower than the values of the bladder pressures when the amplitudes of the pulse wave signals detected synchronously by other transducers of said selected column of transducers are respectively close to maximum and disappearance.

26. The apparatus as defined in claim 24, further comprising a device for displaying transducer position to indicate a detailed position of the optimal transducer in said photoelectric device array.

27. The apparatus as defined in claim 24, further comprising a warning device of transducer position to issue a warning signal when a position of said optimal transducer does not correspond to the center of said photoelectric device array.

28. The apparatus as defined in claim 17, wherein said pressure feeding-measuring system is capable of intermittently measuring the blood pressure of the radial artery according to oscillometric method.

29. The apparatus as defined in claim 17, wherein said pressure feeding-measuring system is capable of continuously measuring the blood pressure of the radial artery according to vascular unloading method.

30. The apparatus as defined in claim 17, wherein said pressure feeding-measuring system is capable of both intermittently measuring the blood pressure of the radial artery according to oscillometric method and continuously measuring the blood pressure of the radial artery according to vascular unloading method; said apparatus further comprising a switching device for controlling said pressure feeding-measuring system to intermittently measure the radial artery blood pressure according to the oscillometric method and to continuously measure the radial artery blood pressure according to the vascular unloading method.

31. The apparatus as defined in claim 17, further comprising;
a pressure bladder adapted to be positioned on the skin above an ulnar artery of the patient for applying external pressure to the ulnar artery,
a pulse transducer for detecting the pulse wave signal of the ulnar artery, and
a switching device for switching the two pressure bladders and pulse transducers to measure either radial arterial blood pressure or ulnar arterial blood pressure.

32. The apparatus as defined in claim 31, further comprising a calibrating device for calibrating a measured ulnar artery blood pressure value according to the measured radial artery blood pressure value.

* * * * *